United States Patent [19]
Gallenkamp et al.

[11] Patent Number: 5,959,119
[45] Date of Patent: Sep. 28, 1999

[54] PROCESS FOR PREPARING 3,5-DIMETHYLISOXAZOLE-4-SULPHONYL CHLORIDE

[75] Inventors: Bernd Gallenkamp; Lothar Rohe, both of Wuppertal, Germany

[73] Assignee: Bayer Aktiengesellschaft, Leverkusen, Germany

[21] Appl. No.: 09/175,817

[22] Filed: Oct. 20, 1998

[30] Foreign Application Priority Data

Oct. 29, 1997 [DE] Germany .................. 197 47 625

[51] Int. Cl.$^6$ .................................................. C07D 261/10
[52] U.S. Cl. ................................................................ 548/243
[58] Field of Search ............................................... 548/243

*Primary Examiner*—Joseph K. McKane
*Attorney, Agent, or Firm*—Joseph C. Gil; Carol Marmo

[57] ABSTRACT

By a novel process, 3,5-dimethylisoxazole-4-sulphonyl chloride is prepared by reacting 3,5-dimethylisoxazole initially with chlorosulphonic acid and then additionally with thionyl chloride at a temperature between 60° C. and 110° C.

3 Claims, No Drawings

PROCESS FOR PREPARING 3,5-DIMETHYLISOXAZOLE-4-SULPHONYL CHLORIDE

The present invention relates to a novel process for preparing the known 3,5-dimethylisoxazole-4-sulphonyl chloride which can be used as an intermediate for preparing active compounds having microbicidal properties.

It is already known that 3,5-dimethylisoxazole-4-sulphonyl chloride can be prepared by reacting 3,5-dimethylisoxazole with chlorosulphonic acid (cf. J. Het. Chem. 18 (1981), 997–1006). However, it is a disadvantage of this process that the desired product is obtained only in relatively low yield.

It has now been found that 3,5-dimethylisoxazole-4-sulphonyl chloride of the formula

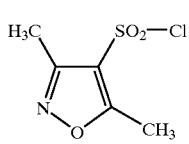

(I)

can be obtained by reacting 3,5-dimethylisoxazole of the formula

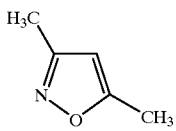

(II)

initially with chlorosulphonic acid and then additionally with thionyl chloride at temperatures between 60° C. and 110° C.

It is extremely surprising that 3,5-dimethyl-isoxazole-4-sulphonyl chloride of the formula (I) can be prepared by the process according to the invention in considerably higher yield than by the prior-art method.

The process according to the invention has a number of advantages. Thus, as already mentioned, it permits the synthesis of 3,5-dimethylisoxazole-4-sulphonyl chloride of the formula (I) in very high yield. It is also favorable that the required reaction components can be prepared in a simple manner and are available even in larger amounts. Finally, it is a further advantage that the practice of the reaction and the isolation of the reaction product is possible without any problems.

If 3,5-dimethylisoxazole is initially reacted with chlorosulphonic acid and thionyl chloride is subsequently added, the course of the process according to the invention can be illustrated by the equation below.

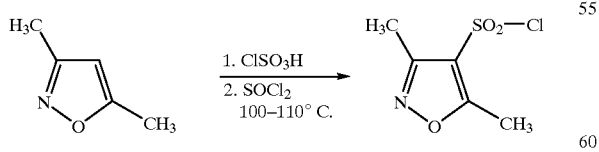

The 3,5-dimethylisoxazole of the formula (II) required as starting material for carrying out the process according to the invention is known (cf. J. Het. Chem. 18 (1981), 997–1006).

The compounds chlorosulphonic acid and thionyl chloride required as reaction components are also known.

The process according to the invention is generally carried out under atmospheric pressure. However, it is also possible to carry out the process under elevated pressure.

When carrying out the process according to the invention, generally from 2 to 10 mol of chlorosulphonic acid and from 1 to 5 mol of thionyl chloride, preferably from 3 to 6 mol of chlorosulphonic acid and from 1.5 to 3 mol of thionyl chloride are employed per mole of 3,5-dimethylisoxazole of the formula (II).

Specifically, the reaction is carried out by reacting 3,5-dimethylisoxazole with chlorosulphonic acid and additionally adding, after a reaction time of from 1 to 3 hours, thionyl chloride. The subsequent work-up is carried out in a customary manner. In general, the reaction mixture is poured onto a mixture of ice and water and the resulting solid product is filtered off with suction and dried.

The 3,5-dimethylisoxazole-4-sulphonyl chloride of the formula (1) which can be prepared by the process according to the invention is known as a useful intermediate for the synthesis of active compounds having microbicidal properties (cf. WO-A 97-06 171).

Thus, it is possible to prepare fungicidally active benzimidazole derivatives of the formula

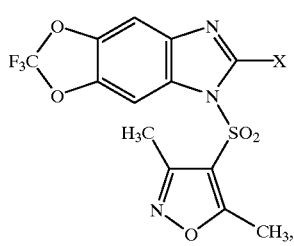

(III)

in which x represents chlorine or bromine, by reacting benzimidazoles of the formula

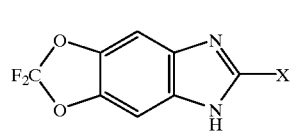

(IV)

in which

X is as defined above with 3,5-dimethylisoxazole-4-sulphonyl chloride of the formula

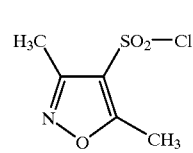

(I)

in the presence of an acid binder, such as sodium hydride or potassium carbonate, and in the presence of a diluent, such as tetrahydrofuran or acetonitrile.

The practice of the process according to the invention is illustrated by the Examples below.

PREPARATION EXAMPLES

Example 1

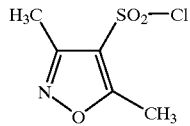

Over a period of 45 minutes, 266 ml (4.0 mol) of chlorosulphonic acid are added dropwise with stirring to 97.2 g (1 mol) of 3,5-dimethylisoxazole which has been heated to 80° C. After the addition has ended, the reaction mixture is stirred at 110° C. for another 2 hours. The mixture is subsequently cooled to 60° C., and 142.8 g (1.2 mol) of thionyl chloride are added dropwise over a period of 30 minutes. The reaction mixture is stirred for another 1.5 hours and slowly heated to 110° C. during this time, and then added dropwise with stirring to a mixture of 1.5 kg of ice and 1 liter of water over a period of 45 minutes. The resulting mixture is stirred for 30 minutes. The solid that is obtained is then filtered off with suction, washed with 1 liter of water and dried. This gives 159.8 g (81.7% of theory) of 3,5-dimethylisoxazole-4-sulphonyl chloride in the form of a solid of melting point 38.3° C.

Comparative Example A

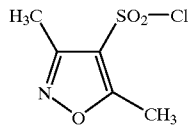

Starting at room temperature, 790 g (6.64 mol) of chlorosulphonic acid are added dropwise with stirring to 161.4 g (1.66 mol) of 3,5-dimethylisoxazole over a period of 90 min, during which the temperature of the reaction mixture rises to 90° C. After the addition has ended, the reaction mixture is heated to 100° C. over a period of 20 min and then stirred at 100° C. for 1.5 hours and subsequently at 110° C. for another 1.5 hours. The resulting mixture is poured onto 2.6 kg of ice. This mixture is allowed to stand at room temperature for 16 hours, and the resulting precipitate is then filtered off with suction and dried. The product is extracted with 200 ml of hot petroleum ether and filtered, and the residue is decocted once more with 50 ml of petroleum ether. The combined petroleum ether phases are cooled to 0 to 5° C. for 5 hours. The resulting precipitate is filtered off with suction and dried. This gives 45.7 g (13.8% of theory) of 3,5-dimethylisoxazole-4-sulphonyl chloride in the form of a solid of melting point 38–39° C.

Use Example I

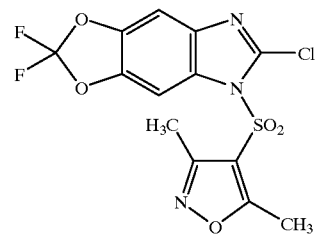

(III-1)

At room temperature, a mixture of 96.6 g (0.4 mol) of 2-chloro-6,6-difluoro[1,3]dioxolo[4,5-f]benzimidazole and 600 ml of acetonitrile is admixed with stirring with 81.6 g (0.6 mol) of pulverized potassium carbonate and stirred at room temperature for 10 minutes. 79.2 g (0.4 mol) of 3,5-dimethyl-isoxazole-4-sulphonyl chloride are subsequently added, and the mixture is stirred at room temperature for a further 20 hours. The reaction mixture is poured into 2 liters of water. The resulting mixture is extracted 3 times with 500 ml of methylene chloride each time. The combined organic phases are dried over sodium sulphate and concentrated under reduced pressure. The residue that remains is chromatographed over silica gel using methylene chloride as mobile phase. This gives 117 g (75% of theory) of 1-(3,5dimethyl-isoxazole-4-sulphonyl)-2-chloro-6,6-difluoro-[1,3]dioxolo-[4,5-f]-benzimidazole in the form of a colorless solid of melting point 128 to 131° C.

Use Example II

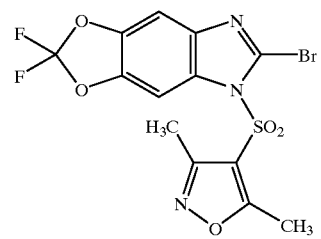

(III-2)

At room temperature, a mixture of 1.4 g (5 mmol) of 2-bromo-6,6-difluoro-[1,3]dioxolo[4,5f]-benzimida and 30 ml of absolute tetrahydrofuran is admixed with stirring with 0.2 g (5 mmol) of sodium hydride (60% strength) and then stirred at room temperature for 30 minutes. 1.0 g (5.5 mmol) of 3,5-dimethylisoxazole-4-sulphonyl chloride is subsequently added, and the mixture is stirred at room temperature for a further 3 hours. For work-up, the reaction mixture is poured into 100 ml of water. The resulting mixture is extracted twice with 50 ml of ethyl acetate each time. The combined organic phases are dried over sodium sulphate and concentrated under reduced pressure. The residue that remains is chromatograped over silical gel using methylene chloride as mobile phase. This gives 1.2 g (75% of theory) of 1-(3,5-dimethylisoxazole-4-sulphonyl)-2-bromo-6,6-difluoro-[1,3]-dioxolo-[4,5]benzimidazole in the form of a colorless solid of melting point 130–143° C.

It will be understood that the specification and examples are illustrative, but not limitative of the present invention and that other present embodiments within the spirit and scope of the invention will suggest themselves to those skilled in the art.

We claim:

1. A process for preparing 3,5-dimethylisoxazole-4-sulphonyl chloride of the formula

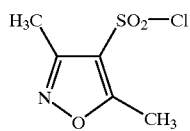

which process comprises reacting 3,5-dimethylisoxazole of the formula

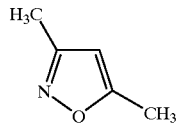

initially with chlorosulphonic acid and then additionally with thionyl chloride at a temperature between 60° C. and 110° C.

2. A process as claimed in claim 1, wherein from 2 to 10 mol of chlorosulphonic acid are employed per mole of 3,5-dimethylisoxazole.

3. A process as claimed in claim 1, wherein from 1 to 5 mol of thionyl chloride are employed per mole of 3,5-dimethylisoxazole.

* * * * *